(12) United States Patent
Beals et al.

(10) Patent No.: US 7,491,697 B2
(45) Date of Patent: Feb. 17, 2009

(54) MUTEINS OF FIBROBLAST GROWTH FACTOR 21

(75) Inventors: John Michael Beals, Indianapolis, IN (US); Christopher Carl Frye, Bargersville, IN (US); Wolfgang Glaesner, Indianapolis, IN (US); Shun Li, Carmel, IN (US); Radhakrishnan Rathnachalam, Carmel, IN (US); Jing Shang, Fishers, IN (US); Beth Ann Strifler, Brownsburg, IN (US); Radmila Micanovic, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 197 days.

(21) Appl. No.: 10/579,510

(22) PCT Filed: Dec. 1, 2004

(86) PCT No.: PCT/US2004/037200

§ 371 (c)(1),
(2), (4) Date: May 16, 2006

(87) PCT Pub. No.: WO2005/061712

PCT Pub. Date: Jul. 7, 2005

(65) Prior Publication Data

US 2007/0142278 A1    Jun. 21, 2007

Related U.S. Application Data

(60) Provisional application No. 60/528,582, filed on Dec. 10, 2003.

(51) Int. Cl.
*C07K 14/50* (2006.01)
*A61K 38/18* (2006.01)

(52) U.S. Cl. .............................. 514/12; 514/2; 530/399
(58) Field of Classification Search ...................... None
See application file for complete search history.

(56) References Cited

U.S. PATENT DOCUMENTS

| 6,716,626 | B1 | 4/2004 | Itoh et al. |
| 2002/0164713 | A1 | 11/2002 | Itoh et al. |
| 2005/0037457 | A1 | 2/2005 | Itoh et al. |
| 2005/0048507 | A1 | 3/2005 | Zhong |

FOREIGN PATENT DOCUMENTS

| WO | WO 01/18172 | 3/2001 |
| WO | WO 01/18209 | 3/2001 |
| WO | WO 01/32678 | 5/2001 |
| WO | WO 01/36640 | 5/2001 |
| WO | WO 01/49849 | 7/2001 |
| WO | WO 01/72957 | 10/2001 |
| WO | WO 01/94587 | 12/2001 |
| WO | WO 03/011213 | 2/2003 |
| WO | WO 03/059270 | 7/2003 |

OTHER PUBLICATIONS

Nishimura, et al., "Identification of a Novel FGF, FGF-21, Preferentially Expressed in the Liver", Biochimica et Biophysica Acta, 1492 (2000), 203-206.

*Primary Examiner*—Christine J Saoud
(74) *Attorney, Agent, or Firm*—Lynn D. Apelgren

(57) ABSTRACT

The present invention relates to novel muteins of human fibroblast growth factor 21 with improved pharmaceutical properties. Both protein and the respective encoding nucleic acid species are disclosed. The invention also embodies vectors and host cells for the propagation of said nucleic acid sequences and the production of said muteins. Also disclosed are methods for treating type 2 diabetes, obesity, metabolic syndrome, and in reducing the mortality and morbidity of critically ill patients.

9 Claims, No Drawings

SEQUENCE LISTING

<160> NUMBER OF SEQ ID NOS: 2

<210> SEQ ID NO 1
<211> LENGTH: 181
<212> TYPE: PRT
<213> ORGANISM: human

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

```
Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
        130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 543
<212> TYPE: DNA
<213> ORGANISM: human

<400> SEQUENCE: 2 cacccatcc   ctgactccag   tcctctcctg   caattcgggg   gccaagtccg   gcagcggtac         60
ctctacacag  atgatgccca   gcagacagaa   gcccacctgg   agatcaggga   ggatgggacg        120 gtgggggcg   ctgctgacca   gagccccgaa   agtctcctgc   agctgaaagc   cttgaagccg        180
ggagttattc  aaatcttggg   agtcaagaca   tccaggttcc   tgtgccagcg   gccagatggg        240
gccctgtatg  gatcgctcca   ctttgaccct   gaggcctgca   gcttccggga   gctgcttctt        300
gaggacggat  acaatgttta   ccagtccgaa   gcccacggcc   tcccgctgca   cctgccaggg        360
aacaagtccc  cacaccggga   ccctgcaccc   cgaggaccag   ctcgcttcct   gccactacca        420
ggcctgcccc  ccgcactccc   ggagccaccc   ggaatcctgg   cccccagcc    cccgatgtg         480 ggctcctcgg  accctctgag   catggtggga   ccttcccagg   gccgaagccc   cagctacgct        540
tcc                                                                              543
```

MUTEINS OF FIBROBLAST GROWTH FACTOR 21

This application claims the benefit of U.S. Provisional Application Ser. No. 60/528,582 filed Dec. 10, 2003, now abandoned.

BACKGROUND OF THE INVENTION

1. Field of the Invention

The present invention relates to the identification of new muteins of fibroblast growth factor 21 that have improved pharmaceutical properties.

2. Description of the Related Art

Fibroblast growth factors are large polypeptides widely expressed in developing and adult tissues (Baird et al., *Cancer Cells,* 3:239-243, 1991) and play crucial roles in multiple physiological functions including angiogenesis, mitogenesis, pattern formation, cellular differentiation, metabolic regulation and repair of tissue injury (McKeehan et al., *Prog. Nucleic Acid Res. Mol. Biol.* 59:135-176, 1998). According to the published literature, the FGF family now consists of at least twenty-three members, FGF-1 to FGF-23 (Reuss et al., *Cell Tissue Res.* 313:139-157 (2003).

Fibroblast growth factor 21 (FGF-21) has been reported to be preferentially expressed in the liver (Nishimura et al., *Biochimica et Biophysica Acta,* 1492:203-206, (2000); WO01/36640; and WO01/18172) and described as a treatment for ischemic vascular disease, wound healing, and diseases associated with loss of pulmonary, bronchia or alveolar cell function and numerous other disorders. More recently, FGF-21 has been shown to stimulate glucose-uptake in mouse 3T3-L1 adipocytes in the presence and absence of insulin, and to decrease fed and fasting blood glucose, triglycerides, and glucagon levels in ob/ob and db/db mice and 8 week old ZDF rats in a dose-dependant manner, thus, providing the basis for the use of FGF-21 as a therapy for treating diabetes and obesity (WO03/011213). In addition, FGF-21 has been shown to be effective in reducing the mortality and morbidity of critically ill patients (WO03/059270).

A significant challenge in the development of protein pharmaceuticals, such as FGF-21, is to cope with their physical and chemical instabilities. The compositional variety and characteristics of proteins define specific behaviors such as folding, conformational stability, and unfolding/denaturation. Such characteristics must be addressed to stabilize proteins when developing pharmaceutical formulation conditions utilizing aqueous protein solutions (Wang, W., *Int. J. of Pharmaceutics,* 18, (1999).

Specifically, in pharmaceutical protein development, antimicrobial preservative agents such as phenol, m-cresol, methylparaben, resorcinol, and benzyl alcohol are necessary in parenteral pharmaceutical formulations that are intended to be a sterile, multi-use formulation. Unfortunately, these compounds often adversely affect the stability of the protein product, triggering association and aggregation, in particular (Maa et al., *Int. J. of Pharmaceutics* 140:155-168 (1996); Lam et al., *Pharm. Res.* 14(6):725-729 (1997)).

FGF-21 will likely be utilized as a multi-use, sterile pharmaceutical formulation. However, it has been determined that preservatives, i.e. m-cresol, have an adverse affect on its stability under these conditions. Clearly, there is a need to develop a stable aqueous protein formulation for the therapeutic protein FGF-21. The present invention overcomes the significant hurdles of physical instabilities with the invention of muteins of FGF-21 that are more stable than wild-type FGF-21 under pharmaceutical formulation conditions. Thus, the muteins of FGF-21 of the present invention provide stable pharmacological protein formulations that are useful for the treatment of type 2 diabetes, obesity, metabolic syndrome, and in reducing the mortality and morbidity of critically ill patients.

SUMMARY OF THE INVENTION

In a first aspect, the present invention provides muteins of human fibroblast growth factor 21, or a biologically active peptide thereof, comprising the substitution with a charged and/or polar but uncharged amino acid for one or more of the following: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152, alanine 154, glutamine 156, glycine 161, serine 163, glycine 170, or serine 172 wherein the numbering of the amino acids is based on SEQ ID NO:1.

A second aspect of the present invention provides muteins of human fibroblast growth factor 21, or a biologically active peptide thereof, comprising the substitution of a cysteine for two or more of the following: arginine 19, tyrosine 20, leucine 21, tyrosine 22, threonine 23, aspartate 24, aspartate 25, alanine 26, glutamine 27, lutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of the amino acids is based on SEQ ID NO:1.

A third aspect of the present invention provides muteins of human FGF-21, or a biologically active peptide thereof, comprising the substitution with any charged and/or polar but uncharged amino acid at any of the amino acid positions indicated in the first embodiment of the present invention in combination with the substitution of a cysteine at two or more amino acid positions indicated in the second embodiment of the invention.

Other embodiments are drawn to polynucleotides encoding the muteins of the first, second, and third embodiments, a vector containing said polynucleotides and a host cell carrying said vector. Another embodiment is drawn to processes to produce a polypeptide, to produce cells capable of producing said polypeptide and to produce a vector containing DNA encoding said polypeptide.

Yet another embodiment is drawn to methods of treating a patient exhibiting one or more of obesity, type 2 diabetes, insulin resistance, hyperinsulinemia, glucose intolerance, hyperglycemia, or metabolic syndrome comprising administering to said patient in need of such treatment a therapeutically effective amount of a human FGF-21 mutein of the first, second, or third embodiment or a pharmaceutical composition thereof.

DETAILED DESCRIPTION OF THE INVENTION

For purposes of the present invention, as disclosed and claimed herein, the following terms are as defined below.

FGF-21 is a 208 amino acid polypeptide containing a 27 amino acid leader sequence. Human FGF-21 has ~79% amino acid identity to mouse FGF-21 and ~80% amino acid identity to rat FGF-21. Human FGF-21 is the preferred polypeptide template for the muteins of the present invention but it is recognized that one with skill in the art could readily make muteins based on an alternative mammalian FGF-21 polypeptide sequence.

The amino acid positions of the muteins of the present invention are determined from the mature human 181 amino acid FGF-21 polypeptide as shown below (SEQ ID NO:1).

```
1                                       10                                      20
His Pro Ile Pro Asp Ser Ser Pro Leu Leu Gln Phe Gly Gly Gln Val Arg Gln Arg Tyr 30                                      40
Leu Tyr Thr Asp Asp Ala Gln Gln Thr Glu Ala His Leu Glu Ile Arg Glu Asp Gly Thr 50                                      60
Val Gly Gly Ala Ala Asp Gln Ser Pro Glu Ser Leu Leu Gln Leu Lys Ala Leu Lys Pro 70                                      80
Gly Val Ile Gln Ile Leu Gly Val Lys Thr Ser Arg Phe Leu Cys Gln Arg Pro Asp Gly 90                                      100
Ala Leu Tyr Gly Ser Leu His Phe Asp Pro Glu Ala Cys Ser Phe Arg Glu Leu Leu Leu 110                                     120
Glu Asp Gly Tyr Asn Val Tyr Gln Ser Glu Ala His Gly Leu Pro Leu His Leu Pro Gly 130                                     140
Asn Lys Ser Pro His Arg Asp Pro Ala Pro Arg Gly Pro Ala Arg Phe Leu Pro Leu Pro 150                                     160
Gly Leu Pro Pro Ala Leu Pro Gln Pro Pro Gly Ile Leu Ala Pro Gln Pro Pro Asp Val 170                                     180
Gly Ser Ser Asp Pro Leu Ser Met Val Gly Pro Ser Gln Gly Arg Ser Pro Ser Tyr Ala

Ser
```

The corresponding DNA sequence coding for the mature human 181 amino acid FGF-21 polypeptide is (SEQ ID NO:2):

```
CACCCCATCCCTGACTCCAGTCCTCTCCTGCAATTCGGGGGCCAAGTCCG
GCAGCGGTACCTCTACACAGATGATGCCCAGCAGACAGAAGCCCACCTGG
AGATCAGGGAGGATGGGACGGTGGGGGGCGCTGCTGACCAGAGCCCCGAA
AGTCTCCTGCAGCTGAAAGCCTTGAAGCCGGGAGTTATTCAAATCTTGGG
AGTCAAGACATCCAGGTTCCTGTGCCAGCGGCCAGATGGGGCCCTGTATG
GATCGCTCCACTTTGACCCTGAGGCCTGCAGCTTCCGGGAGCTGCTTCTT
GAGGACGGATACAATGTTTACCAGTCCGAAGCCCACGGCCTCCCGCTGCA
CCTGCCAGGGAACAAGTCCCCACACCGGGACCCTGCACCCCGAGGACCAG
CTCGCTTCCTGCCACTACCAGGCCTGCCCCCCGCACTCCCGGAGCCACCC
GGAATCCTGGCCCCCCAGCCCCCCGATGTGGGCTCCTCGGACCCTCTGAG
CATGGTGGGACCTTCCCAGGGCCGAAGCCCCAGCTACGCTTCC
```

One skilled in the art of expression of proteins will recognize that methionine or methionine-arginine sequence can be introduced at the N-terminus of the mature sequence (SEQ ID NO: 1) for expression in *E. coli* and are contemplated within the context of this invention.

Amino acids are identified using the three-letter code or alternatively could be designated using the standard one letter code. Mutations are designated by the three-letter code for the original amino acid, followed by the amino acid number, followed by the three-letter code for the replacement amino acid. The numerical designations of each mutein is based on the 181 amino acid sequence of mature, wild-type, human FGF-21. For example, a substitution for leucine at position 139 (i.e. Leu139) with the negatively charged amino acid, glutamate (Glu) is designated as Leu139Glu or L139E. In a similar fashion, the double substitution for isoleucine at position 152 and serine at position 163 (Ile152, Ser163) with the negatively charged amino acid, glutamate (Glu) is designated as Ile152Glu/Ser163Glu, I152E/S163E or I152E-S163E.

A human FGF-21 mutein is defined as comprising human FGF-21 in which at least one amino acid of the wild-type mature protein has been substituted by another amino acid. Generally speaking, a mutein possesses some modified property, structural or functional, of the wild-type protein. For example, the mutein may have enhanced or improved physical stability in concentrated solutions (e.g., less hydrophobic mediated aggregation), while maintaining a favorable bioactivity profile. The mutein may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. Accordingly, muteins with enhanced pharmaceutical stability when compared to wild-type FGF-21, have improved physical stability in concentrated solutions under both physiological and preserved pharmaceutical formulation conditions, while maintaining biological potency. As used herein, these terms are not limiting, it being entirely possible that a given mutein has one or more modified properties of the wild-type protein.

A "biologically active peptide" is defined as a peptide of a mutein of the present invention that maintains the modified property(s) and the biological potency of the mutein.

A "therapeutically-effective amount" is the minimal amount of an active agent necessary to impart therapeutic benefit to a patient. For example, a "therapeutically-effective amount" to a patient exhibiting, suffering or prone to suffer or to prevent it from suffering from type 2 diabetes, obesity, or metabolic syndrome is such an amount which induces, ameliorates or otherwise causes an improvement in the pathological symptoms, disease progression, physiological conditions associated with or resistance to succumbing to the aforementioned disorders. For the purposes of the present invention a "subject" or "patient" is preferably a human, but can also be an animal, more specifically, a companion animal (e.g., dogs, cats, and the like), farm animals (e.g., cows, sheep, pigs, horses, and the like) and laboratory animals (e.g., rats, mice, guinea pigs, and the like).

"Type 2 diabetes" is characterized by excess glucose production in spite of the availability of insulin, and circulating glucose levels remain excessively high as a result of inadequate glucose clearance.

"Glucose intolerance" can be defined as an exceptional sensitivity to glucose.

"Hyperglycemia" is defined as an excess of sugar (glucose) in the blood.

"Hypoglycemia", also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity", in terms of the human subject, can be defined as that body weight over 20 percent above the ideal body weight for a given population (R. H. Williams, Textbook of Endocrinology, 1974, p. 904-916).

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dL in the bloodstream; low HDL—less than 40 mg/dl; and, blood pressure of 130/85 or higher.

The critically ill patients encompassed by the present invention generally experience an unstable hypermetabolic state. This unstable metabolic state is due to changes in substrate metabolism, which may lead to relative deficiencies in some nutrients. Generally there is an increased oxidation of both fat and muscle.

Moreover, critically ill patients are preferably patients that experience systemic inflammatory response syndrome or respiratory distress. A reduction in morbidity means reducing the likelihood that a critically ill patient will develop additional illnesses, conditions, or symptoms or reducing the severity of additional illnesses, conditions, or symptoms. For example reducing morbidity may correspond to a decrease in the incidence of bacteremia or sepsis or complications associated with multiple organ failure.

"Systemic inflammatory response syndrome (SIRS)" as used herein describes an inflammatory process associated with a large number of clinical conditions and includes, but is not limited to, more than one of the following clinical manifestations: (1) a body temperature greater than 38° C. or less than 36° C.; (2) a heart rate greater than 90 beats per minute; (3) tachypnea, manifested by a respiratory rate greater than 20 breaths per minute, or hyperventilation, as indicated by a $PaCO_2$ of less than 32 mm Hg; and (4) an alteration in the white blood cell count, such as a count greater than 12,000/cu mm, a count less than 4,000/cu mm, or the presence of more than 10% immature neutrophils. These physiologic changes should represent an acute alteration from baseline in the absence of other known causes for such abnormalities, such as chemotherapy, induced neutropenia, and leukopenia.

"Sepsis" as used herein is defined as a SIRS arising from infection. Noninfectious pathogenic causes of SIRS may include pancreatitis, ischemia, multiple trauma and tissue injury, i.e. crushing injuries or severe burns, hemorrhagic shock, immune-mediated organ injury, and the exogenous administration of such putative mediators of the inflammatory process as tumor necrosis factor and other cytokines.

Septic shock and multi-organ dysfunction are major contributors to morbidity and mortality in the ICU setting. Sepsis is associated with and mediated by the activation of a number of host defense mechanisms including the cytokine network, leukocytes, and the complement cascade, and coagulation/fibrinolysis systems including the endothelium. Disseminated intravascular coagulation (DIC) and other degrees of consumption coagulopathy associated with fibrin deposition within the microvasculature of various organs are manifestations of sepsis/septic shock. The downstream effects of the host defense response on target organs is an important mediator in the development of the multiple organ dysfunction syndrome (MODS) and contributes to the poor prognosis of patients with sepsis, severe sepsis, and sepsis complicated by shock.

"Respiratory distress" as used herein denotes a condition wherein patients have difficulty breathing due to some type of pulmonary dysfunction. Often these patients exhibit varying degrees of hypoxemia that may or may not be refractory to treatment with supplemental oxygen.

Respiratory distress may occur in patients with impaired pulmonary function due to direct lung injury or may occur due to indirect lung injury such as in the setting of a systemic process. In addition, the presence of multiple predisposing disorders substantially increases the risk, as does the presence of secondary factors such as chronic alcohol abuse, chronic lung disease, and a low serum pH.

Some causes of direct lung injury include pneumonia, aspiration of gastric contents, pulmonary contusion, fat emboli, near drowning, inhalation injury, high altitude and reperfusion pulmonary edema after lung transplantation or pulmonary embolectomy. Some causes of indirect lung injury include sepsis, severe trauma with shock and multiple transfusions, cardiopulmonary bypass, drug overdose, acute pancreatitis, and transfusions of blood products.

One class of pulmonary disorders that causes respiratory distress are associated with the syndrome known as Cor Pulmonale. These disorders are associated with chronic hypoxemia resulting in raised pressure within the pulmonary circulation called pulmonary hypertension. The ensuing pulmonary hypertension increases the work-load of the right ventricle, thus leading to its enlargement or hypertrophy. Cor Pulmonale generally presents as right heart failure defined by a sustained increase in right ventricular pressures and clinical evidence of reduced venous return to the right heart.

"Chronic obstructive pulmonary diseases" (COPDs), which include emphysema and chronic bronchitis also cause respiratory distress and are characterized by obstruction to air flow. COPDs are the fourth leading cause of death and claim over 100,000 lives annually.

"Acute respiratory distress syndrome" (ARDS) is generally progressive and characterized by distinct stages. The syndrome is generally manifested by the rapid onset of respiratory failure in a patient with a risk factor for the condition. Arterial hypoxemia that is refractory to treatment with supplemental oxygen is a characteristic feature. There may be alveolar filling, consolidation, and atelectasis occurring in dependent lung zones; however, non-dependent areas may have substantial inflammation. The syndrome may progress to fibrosing alveolitis with persistent hypoxemia, increased alveolar dead space, and a further decrease in pulmonary compliance. Pulmonary hypertension, which results from damage to the pulmonary capillary bed, may also develop.

The first preferred aspect of the invention comprises muteins of human FGF-21 in which substitution means that any charged and/or polar but uncharged amino acid replaces at least one of the following: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152, alanine 154, glutamine 156, glycine 161 serine 163, glycine 170, or serine 172, wherein the numbering of the amino acids is based on SEQ ID NO:1. A charged amino acid is defined as a positively or negatively charged amino acid. A positively charged amino acid is defined to include histadine, lysine, arginine, and non-naturally occurring analogs thereof (e.g., gamma aminobutyric acid, omithine, etc.). A negatively charged amino acid is defined to included aspartate, glutamate, and non-naturally occurring analogs thereof (e.g., aminoadipic acid). A polar but uncharged amino acid is defined to include serine, threonine, asparagine, glutamine, and non-naturally occurring analogs thereof. The most preferred muteins of the first embodiment are Gln54Glu, Leu139Glu, Ala145Glu, Leu146Glu, Ile152Glu, Gln156Glu, Ser163Glu, and Ile152Glu-Ser163Glu.

The second aspect of the present invention provides muteins of human FGF-21, or a biologically active peptide thereof, comprising the substitution of a cysteine for two or more of the following: arginine 19, tyrosine 20, leucine 21, tyrosine 22, threonine 23, aspartate 24, aspartate 25, alanine 26, glutamine 27, lutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of the amino acids is based on SEQ ID NO:1.

One skilled in the art will also recognize that the native cysteines, cysteine 75 and cysteine 93, could also be utilized as loci to introduce a novel disulfide bond that may impart improved properties. Specifically contemplated is the introduction of a cysteine substitution at serine 85 or phenylalanine 73, coupled with a concomitant change at either cysteine 93 or cysteine 75, respectively, wherein the latter sites are replaced with any other amino acid.

Naturally occurring disulfide bonds, as provided by cysteine residues, generally increase thermodynamic stability of proteins. Successful examples of increased thermodynamic stability, as measured in increase of the melting temperature, are multiple disulfide-bonded mutants of the enzymes T4 lysozyme (Matsumura, et al., *PNAS* 86:6562-6566 (1989)) and barnase (Johnson et al., *J. Mol. Biol.* 268:198-208 (1997)). An aspect of the present invention is the premise that constraining the flexibility of the 118-134 amino acid loop of FGF-21 by disulfide bonds enhances the physical stability of FGF-21 in the presence of a preservative, presumably by limiting access of the preservative to the hydrophobic core of the protein.

Muteins of FGF-21 with engineered disulfide bonds, in addition to the naturally occurring one at Cys75-Cys93, are as follows: Gln76Cys-Ser109Cys, Cys75-Ser85Cys, Cys75-Ala92Cys, Phe73Cys-Cys93, Ser123Cys-His125-Cys, Asp102Cys-Tyr104Cys, Asp127Cys-Gly132Cys, Ser94Cys-Glu110Cys, Pro115Cys-His117Cys, Asn121Cys-Asp127Cys, Leu100Cys-Asp102Cys, Phe95Cys-Tyr107Cys, Arg19Cys-Pro138Cys, Tyr20Cys-Leu139Cys, Tyr22Cys-Leu137Cys, Arg77Cys-Asp79Cys, Pro90Cys-Ala92Cys, Glu50Cys-Lys69Cys, Thr23Cys-Asp25Cys, Ala31Cys-Gly43Cys, Gln28Cys-Gly43Cys, Thr23Cys-Gln28Cys, Val41Cys-Leu82Cys, Leu58Cys-Val62Cys, Gln54Cys-Leu66Cys, Ile35Cys-Gly67Cys, Gly67Cys-Arg72Cys, Ile35Cys-Gly84Cys, Arg72Cys-Gly84Cys, or Arg77Cys-Ala81Cys, wherein the numbering of the amino acids is based on SEQ ID NO:1. Preferred muteins with engineered disulfide bonds are Tyr22Cys-Leu139Cys; Asp24Cys-Arg135Cys; Leu118Cys-Gly132Cys; His117Cys-Pro130Cys; His117Cys-Ala129Cys; Leu82Cys-Pro119Cys; Gly80Cys-Ala129Cys; Gly43Cys-Pro124Cys; Gly42Cys-Arg126Cys; Gly42Cys-Pro124Cys; Gln28Cys-Pro124Cys; Gln27Cys-Ser123Cys; Ala26Cys-Lys122Cys; or Asp25Cys-Lys122Cys. Most preferred muteins with engineered disulfide bonds are Leu118Cys-Ala134Cys; Leu21Cys-Leu33Cys; Ala26Cys-Lys122Cys; Leu21Cys-Leu33Cys/Leu118Cys-Ala134Cys The third aspect of the present invention provides muteins of human FGF-21, or a biologically active peptide thereof, comprising a substitution of any charged and/or polar but uncharged amino acid at any of the amino acid positions indicated in the first embodiment of the present invention combined with the substitution of a cysteine at two or more amino acid positions indicated in the second embodiment of the invention.

It is well known in the art that a significant challenge in the development of protein pharmaceuticals is to deal with the physical and chemical instabilities of proteins. This is even more apparent when a protein pharmaceutical formulation is intended to be a multiple use, injectable formulation requiring a stable, concentrated and preserved solution, while maintaining a favorable bioactivity profile. Detailed biophysical characterization of wild-type FGF-21 established that a concentrated protein solution (>5 mg/ml), when exposed to stress conditions, such as high temperature or low pH, lead to accelerated association and aggregation (i.e., poor physical stability and biopharmaceutical properties). Exposure of a concentrated protein solution of FGF-21 to pharmaceutical preservatives (e.g., m-cresol) also had a negative impact on physical stability.

Therefore, an embodiment of the present invention is to enhance physical stability of concentrated solutions, while maintaining chemical stability and biological potency, under both physiological and preserved formulation conditions. It is thought that association and aggregation may result from hydrophobic interactions, since, at a given protein concentration, temperature, and ionic strength have considerable impact on physical stability. For the most part, non-conserved, presumed surface exposed amino acid residues were targeted. The local environment of these residues was analyzed and, those that were not deemed structurally important were selected for mutagenesis. One method to initiate specific changes is to further decrease the pI of the protein by introducing glutamic acid residues ("glutamic acid scan"). It is hypothesized that the introduction of charged substitutes would inhibit hydrophobic-mediated aggregation via charge-charge repulsion and potentially improve preservative compatibility. In addition, one skilled in the art would also recognize that with sufficient degree of mutagenesis the pI could be shifted into a basic pH range by the introduction of positive charge with or without concomitant decrease in negative charge, thus allowing for charge-charge repulsion.

Although the embodiments of the present invention concern the physical and chemical stability under both physiological and preserved pharmaceutical formulation conditions, maintaining the biological potency of the muteins as compared to wild-type FGF-21 is an important factor of consideration as well. Therefore, the biological potency of the muteins of the present invention is defined by the ability of the muteins to affect glucose uptake as measured in the in vitro 3T3-L1 cell assay (Example 4) and/or the lowering of plasma glucose levels, as well as, plasma triglycerides, as measured in vivo in the ob/ob mouse assay (Example 5).

The muteins of FGF-21 administered according to this invention may be generated and/or isolated by any means known in the art. The most preferred method for producing the mutein is through recombinant DNA methodologies and is well known to those skilled in the art. Such methods are described in *Current Protocols in Molecular Biology* (John Wiley & Sons, Inc.), which is incorporated herein by reference.

Additionally, the preferred embodiments include a biologically active peptide derived from the mutein described herein. Such a peptide will contain at least one of the substitutions described and the mutein will possess biological activity. The peptide may be produced by any and all means known to those skilled in the art, examples of which included but are not limited to enzymatic digestion, chemical synthesis or recombinant DNA methodologies.

It is established in the art that fragments of peptides of certain fibroblast growth factors are biologically active. See for example, Baird et al., *Proc. Natl. Acad. Sci* (USA) 85:2324-2328 (1988), and *J. Cell. Phys. Suppl.* 5:101-106 (1987). Therefore, the selection of fragments or peptides of the mutein is based on criteria known in the art. For example, it is known that dipeptidyl peptidase IV (DPP-IV) is a serine type protease involved in inactivation of neuropeptides, endocrine peptides, and cytokines (Damme et al. *Chem. Immunol.* 72: 42-56, (1999)). The N-terminus of FGF-21 (His-ProIlePro) contains two dipeptides that could potentially be substrates to DPP-IV, resulting in a fragment of FGF-21 truncated at the N-terminus by 4 amino acids. Unexpectedly, this fragment of wild-type FGF-21 has been demonstrated to retain biological activity (Table 1), thus, muteins of the present invention truncated at the N-terminus by up to 4 amino acids, is an embodiment of the present invention.

The present invention also encompasses polynucleotides encoding the above-described muteins that may be in the form of RNA or in the form of DNA, which DNA includes cDNA, genomic DNA, and synthetic DNA. The DNA may be double-stranded or single-stranded. The coding sequences that encode the muteins of the present invention may vary as a result of the redundancy or degeneracy of the genetic code.

The polynucleotides that encode for the muteins of the present invention may include the following: only the coding sequence for the mutein, the coding sequence for the mutein and additional coding sequence such as a functional polypeptide, or a leader or secretory sequence or a pro-protein sequence; the coding sequence for the mutein and non-coding sequence, such as introns or non-coding sequence 5' and/or 3' of the coding sequence for the mutein. Thus the term "polynucleotide encoding a mutein" encompasses a polynucleotide that may include not only coding sequence for the mutein but also a polynucleotide, which includes additional coding and/or non-coding sequence.

The present invention further relates to variants of the described polynucleotides that encode for fragments, analogs and derivatives of the polypeptide that contain the indicated substitutions. The variant of the polynucleotide may be a naturally occurring allelic variant of the human FGF-21 sequence, a non-naturally occurring variant, or a truncated variant as described above. Thus, the present invention also includes polynucleotides encoding the muteins described above, as well as variants of such polynucleotides, which variants encode for a fragment, derivative or analog of the disclosed mutein. Such nucleotide variants include deletion variants, substitution variants, truncated variants, and addition or insertion variants as long as at least one of the indicated amino acid substitutions of the first or second embodiments is present.

The polynucleotides of the present invention will be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences. The FGF-21 mutein can be expressed in mammalian cells, insect, yeast, bacterial or other cells under the control of appropriate promoters. Cell free translation systems can also be employed to produce such proteins using RNAs derived from DNA constructs of the present invention.

*E. coli* is a prokaryotic host useful particularly for cloning the polynucleotides of the present invention. Other microbial hosts suitable for use include *Bacillus subtilus, Salmonella typhimurium*, and various species of *Serratia, Pseudomonas, Streptococcus*, and *Staphylococcus*, although others may also be employed as a matter of choice. In these prokaryotic hosts, one can also make expression vectors, which will typically contain expression control sequences compatible with the host cell (e.g., an origin of replication). In addition, any of a number of well-known promoters may be present, such as the lactose promoter system, a tryptophan (trp) promoter system, a beta-lactamase promoter system, or a promoter system from phages lambda or T7. The promoters will typically control expression, optionally with an operator sequence, and have ribosome binding site sequences and the like, for initiating and completing transcription and translation.

One skilled in the art of expression of proteins will recognize that methionine or methionine-arginine sequence can be introduced at the N-terminus of the mature sequence (SEQ ID NO: 1) for expression in *E. coli* and are contemplated within the context of this invention. Thus, unless otherwise noted, muteins of the present invention expressed in *E. coli* have a methionine sequence introduced at the N-terminus.

Other microbes, such as yeast or fungi, may also be used for expression. *Pichia pastoris, Saccharomyces cerevisiae, Schizosaccharomyces pombe*, and *Pichia angusta* are examples of preferred yeast hosts, with suitable vectors having expression control sequences, such as promoters, including 3-phosphoglycerate kinase or other glycolytic enzymes, and an origin of replication, termination sequences and the like as desired. *Aspergillus niger, Trichoderma reesei*; and *Schizophyllum commune*, are examples of fungi hosts, although others may also be employed as a matter of choice.

Mammalian tissue cell culture may also be used to express and produce the polypeptides of the present invention. Eukaryotic cells are actually preferred, because a number of suitable host cell lines capable of secreting intact muteins have been developed in the art, and include the CHO cell lines, various COS cell lines, NS0 cells, Syrian Hamster Ovary cell lines, HeLa cells, or human embryonic kidney cell lines (i.e. BEK293, HEK293EBNA).

Expression vectors for these cells can include expression control sequences, such as an origin of replication, a promoter, an enhancer, and necessary processing information sites, such as ribosome binding sites, RNA splice sites, polyadenylation sites, and transcriptional terminator sequences. Preferred expression control sequences are promoters derived from SV40, adenovirus, bovine papilloma virus, cytomegalovirus, Raus sarcoma virus, and the like. Preferred polyadenylation sites include sequences derived from SV40 and bovine growth hormone.

The vectors containing the polynucleotide sequences of interest (e.g., the muteins of FGF-21 and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, NY (1982). The purification step(s) selected will depend, for example, on the nature of the production process used for the muteins of FGF-21.

The FGF-21 mutein-containing compositions should be formulated and dosed in a fashion consistent with good medical practice, taking into account the clinical condition of the patient, the site of delivery of the FGF-21 mutein composition, the method of administration, the scheduling of administration, and other factors known to practitioners. The "therapeutically effective amount" of the FGF-21 mutein for purposes herein is thus determined by such considerations The pharmaceutical compositions of the FGF-21 muteins and of the present invention may be administered by any means that achieve the generally intended purpose: to treat type 2 diabetes, obesity, metabolic syndrome, or critically ill patients. The term "parenteral" as used herein refers to modes of administration that include intravenous, intramuscular, intraperitoneal, intrasternal, subcutaneous, and intraarticular injection and infusion. The dosage administered will be dependent upon the age, health, and weight of the recipient, kind of concurrent treatment, if any, frequency of treatment, and the nature of the effect desired. Compositions within the scope of the invention include all compositions wherein an FGF-21 mutein is present in an amount that is effective to achieve the desired medical effect for treatment type 2 diabetes, obesity, or metabolic syndrome. While individual needs may vary from one patient to another, the determination of the optimal ranges of effective amounts of all of the components is within the ability of the clinician of ordinary skill.

The muteins of FGF-21 of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [*Remington's Pharmaceutical Sciences* 16th edition (1980)]. The muteins of the present invention may be combined with a pharmaceutically acceptable buffer, and the pH adjusted to provide acceptable stability, and a pH acceptable for administration.

For parenteral administration, in one embodiment, the FGF-21 muteins are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising an FGF-21 mutein, as determined by good medical practice and the clinical condition of the individual patient. A typical dose range for the FGF-21 muteins of the present invention will range from about 0.01 mg per day to about 1000 mg per day for an adult. Preferably, the dosage ranges from about 0.1 mg per day to about 100 mg per day, more preferably from about 1.0 mg/day to about 10 mg/day. Most preferably, the dosage is about 1-5 mg/day. The appropriate dose of an FGF-21 mutein administered will result in lowering blood glucose levels and increasing energy expenditure by faster and more efficient glucose utilization, and thus is useful for treating type 2 diabetes, obesity and metabolic syndrome.

In addition, because hyperglycemia and insulin resistance are common in critically ill patients given nutritional support, some ICUs administer insulin to treat excessive hyperglycemia in fed critically ill patients. In fact, recent studies document the use of exogenous insulin to maintain blood glucose at a level no higher than 110 mg per deciliter reduced morbidity and mortality among critically ill patients in the surgical intensive care unit, regardless of whether they had a history of diabetes (Van den Berghe, et al. *N Engl J Med.*, 345(19):1359, (2001)). Thus, muteins of FGF-21 of the present invention are uniquely suited to help restore metabolic stability in metabolically unstable critically ill patients. Muteins of FGF-21 are unique in that they stimulate glucose uptake and enhances insulin sensitivity but do not induce hypoglycemia.

In another aspect of the present invention, muteins of FGF-21 for use as a medicament for the treatment of type 2 diabetes, obesity, metabolic syndrome, or critically ill patients is contemplated.

Having now described the present invention in detail, the same will be more clearly understood by reference to the following examples, which are included herewith for purposes of illustration only and are not intended to be limiting of the invention.

All patents and publications referred to herein are expressly incorporated by reference.

EXAMPLE 1

Expression and Purification of FGF-21 Muteins in *E. coli*

The bacterial expression vector pET30a is used for bacterial expression in this example. (Novagen, Inc., Madison, Wis.)). pET30a encodes kanamycin antibiotic resistance gene and contains a bacterial origin of replication ("ori"), a strong T7 phage-IPTG inducible promoter, a ribosome binding site ("RBS"), and suitable MCS with a number of unique resrtiction endonuclease cleavage sites. Conveniently for purification purpose, the vector can encode His- and S-tags for N-terminal peptide fusions, as well as, a C-terminal His-tag fusion. However, for purposes of the present invention, the cDNA encoding FGF-21 variants is inserted between restriction sites NdeI and BamHI, respectively, and the resulting construct does not take advatrage of either of the described tags.

The nucleic acid sequence encoding the FGF-21 mutein, lacking the leader sequence but substituted with a methionine residue, is amplified from a cDNA clone using PCR oligonucleotide primers, which anneal to the 5' and 3' ends of the open reading frame. Additional nucleotides, containing recognition sites for restriction enzymes NdeI and BamHI, are added to the 5' and 3' sequences, respectively.

For cloning, the 5' forward and 3' reverse PCR primers have nucleotides corresponding or complementary to a portion of the coding sequence of the FGF-21 mutein-encoding nucleic acid according to methods known in the art. One of ordinary skill in the art would appreciate that the point in a polynucleotide sequence where primers begin can be varied.

The amplified nucleic acid fragments and the vector pET30a are digested with NdeI and BamHI restriction enzymes and the purified digested DNA fragments are then ligated together. Insertion of FGF-21 mutein-encoding DNA into the restricted pET30a vector places the FGF-21 mutein polypeptide coding region including its associated stop codon downstream from the IPTG-inducible promoter and in-frame with an initiating ATG codon. The associated stop codon, TAG, prevents translation of the six-histidine codons downstream of the insertion point.

The ligation mixture is transformed into competent E. coli cells using standard procedures such as those described in Current Protocols in Molecular Biology (John Wiley & Sons, Inc.).

Transformation reactions are plated on LB/Kanamycin plates and after an overnight growth transformants are picked for plasmid preparations or lysed in situ for screening by PCR. Positive recombinant plasmids, containing desired FGF-21 variant inserts, are identified by restriction analysis followed by DNA sequence analysis. Those plasmids are subsequently used to transform expression strains and protein production.

E. coli strains BL21(DE3), BL21(DE3)STAR or BL21 (DE3) RP, are used for expressing FGF-21 muteins. These strains, which are only some of many that are suitable for expressing FGF-21 muteins, are available commercially from Novagen, Inc., Invitrogen and Stratagen, respectively. Transformants are identified by their ability to grow on LB plates in the presence of kanamycin.

Clones containing the desired constructs are grown overnight (o/n) in liquid culture in LB media supplemented with kanamycin (30 µg/ml). The o/n culture is used to inoculate a large culture, at a dilution of approximately 1:25 to 1:250. The cells are grown to an optical density of 0.6 ("OD600") at 600 nm. Isopropyl-b-D-thiogalactopyranoside ("IPTG") is then added to a final concentration of 1 mM to induce transcription from the lac repressor sensitive promoter, by inactivating the laci repressor. Cells subsequently are incubated further for 3 to 12 hours. Cells are then harvested by centrifugation, pellets washed with 50 mM Tris buffer, pH 8.0 and stored at −20° C. until purification. The FGF-21 muteins are expressed in the insoluble fraction i.e. inclusion bodies (or granules) of E. coli. Although the expression level may vary from variant-to-variant, a typically observed level for the wild-type (WT) FGF-21 protein is 50 mg/L. The subsequent purification process starts with solubilization of the granules and refolding of the variants followed by four chromatographic steps.

To purify the FGF-21 muteins from E coli, the granules are solubilized in 50 mM Tris, pH 9.0, 7M Urea and 1 mM DTT through a pH ramp to pH 11.0, at room temperature for 1 hour with stirring. The protein is then captured on a Q-Sepharose column using the same buffer described above, and eluted with a linear gradient of 0-400 mM NaCl. The Q-Sepharose pool is then treated with 10 mM DTT, for two hours, at RT, to reduce all disulfide bonds. The pool is then diluted 10-fold so that the buffer concentration is as follows: 50 mM Tris, pH 9.0, 7 M Urea, 10 mM Cysteine, 1 mM DTT with a protein concentration of approximately 250-500 µg/ml. After another two-hour incubation under reducing conditions at RT, to obtain the protein in a free disulfide form, the pool is then dialyzed into 20 mM glycine, pH 9.0 for approximately 48 hours so that the correct disulfide bonds can be formed.

Reversed-phase HPLC chromatography, on a Vydac C18 column and 0.1% TFA/0-50% $CH_3CN$ as a mobile phase is used as an initial purification step. This column is used to concentrate FGF-21 or the FGF-21 muteins and removes contaminating endotoxin.

The following purification step is size exclusion chromatography on a Superdex 35/600 column performed in 1×PBS buffer, pH7.4. At this step FGF-21 muteins are ~95% pure. The last step involves MonoQ chromatography in 50 mM Tris, pH 8.0 and elution with a linear gradient of 0-300 mM NaCl, which usually yields >97% pure protein.

The above described 4-column step purification scheme was used for all the FGF-21 muteins and produced stable preparations.

EXAMPLE 2

Expression and Purification of FGF-21 Muteins in HEK293EBNA Cells

Alternatively, FGF-21 muteins can be produced in a mammalian cell expression system such as HEK293EBNA cells (EdgeBiosystems, Gaiethersburg, Md.). FGF-21 muteins are subcloned in the proprietary expression vector representing a modification of commercially available pEAK10, between NheI and XbaI restriction sites in the MCS. The cDNA sequence encoding mature FGF-21 is fused in frame with the Igκ leader sequence to enhance secretion of the desired product in the tissue culture media. The expression is driven by the strong viral CMV promoter. HEK293EBNA cells are transiently transfected using a standard transfection reagent such as Fugene (Roche Diagnostics, Indianapolis, Ind.) and the appropriate amount of recombinant plasmid, either as a monolayer or suspension culture, at the adequate cell density. Cells are incubated at 37° C. and 5% $CO_2$, in serum free media, and collections are made every day for 5 days. Typically the expression level in the HEK239EBNA suspension culture is ~30 mg/L. The expression of human FGF-21 in mammalian cells yields the natural N-terminus sequence of HPIP, i.e. without a methionine residue at the N-terminus. It was discovered that enzymatically treating FGF-21 from HEK239EBNA cells with DPP-IV (porcine kidney, SIGMA St Louis) resulted in truncation of the N-terminus by four amino acids. When assayed in the mouse 3T3-L1 adipocyte assay (see Example 4), this truncated variant of FGF-21 stimulates glucose uptake at a comparable level to that of wild-type FGF-21 (Table 1).

EXAMPLE 3

Expression and Purification of FGF-21 Muteins in Yeast

Yet another expression system for production of FGF-21 muteins is yeast, such as *Pichia pastoris*, *Pichia methanolica* or *Saccharomyces cerevisiae*. For production in *Pichia pastoris* a commercially available system (Invitrogen, Carlsbad, Calif.) uses vectors with the powerful AOX1 (alcohol oxidase) promoters to drive high-level expression of recombinant proteins. Alternatively, vectors that use the promoter from the GAP gene (glyceraldehyde-3-phosphate dehydrogenase) are available for high level constitutive expression. The multi-copy *Pichia* expression vectors allows one to obtain strains with multiple copies of the gene of interest integrated into the genome. Increasing the number of copies of the gene of interest in a recombinant *Pichia* strain can increase protein expression levels. Yet another yeast expression system is *Saccharomyces cerevisiae*. Expression vectors contain the promoter and enhancer sequences from the GAL1 gene. The GAL1 promoter is one of the most widely used yeast promoters because of its strong transcriptional activity upon induction with galactose.

Analytical characterization (mass spectrum analyses) indicates that the FGF-21 expressed in *Pichia pastoris* is truncated (up to four amino acid removal [HisProIlePro] at the N-terminus, designated hereinafter as des-HPIP). When assayed in the mouse 3T3-L1 adipocyte assay (see Example 4), this truncated variant of FGF-21 stimulates glucose uptake at the same level as wild-type FGF-21 (Table 1).

EXAMPLE 4

Glucose Uptake in Mouse 3T3-L1 Adipocytes

3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, two days after cells reached confluency (referred as day 0), cells are exposed to differentiation medium (DM) containing 10% fetal bovine serum, 10 µg/ml of insulin, 1 µM dexamethasone, and 0.5 µM isobutylmethylxanthine, for 48 h. Cells then are maintained in post differentiation medium containing 10% fetal bovine serum, and 10 µg/ml of insulin.

Glucose Transport Assay—Hexose uptake, as assayed by the accumulation of 0.1 mM 2-deoxy-D-[$^{14}$C]glucose, is measured as follows: 3T3-L1 adipocytes in 12-well plates are washed twice with KRP buffer (136 mM NaCl, 4.7 mM KCl, 10 mM NaPO$_4$, 0.9 mM CaCl$_2$, 0.9 mM MgSO$_4$, pH 7.4) warmed to 37° C. and containing 0.2% BSA, incubated in Leibovitz's L-15 medium containing 0.2% BSA for 2 h at 37° C. in room air, washed twice again with KRP containing, 0.2% BSA buffer, and incubated in KRP, 0.2% BSA buffer in the absence (Me$_2$SO only) or presence of wortmannin for 30 min at 37° C. in room air. Insulin is then added to a final concentration of 100 nM for 15 min, and the uptake of 2-deoxy-D-[$^{14}$C]glucose is measured for the last 4 min. Non-specific uptake, measured in the presence of 10 µM cytochalasin B, is subtracted from all values. Protein concentrations are determined with the Pierce bicinchoninic acid assay. Uptake is measured routinely in triplicate or quadruplicate for each experiment.

In vitro potency is normalized to the in vitro activity of wild-type FGF-21, which is given a designation of 1.0 and used as a positive control. The in vitro potency of muteins of FGF-21 of the present invention is compared to wild-type FGF-21 in Table 1. As indicated in Table 1, the muteins of the present invention maintained biological potency to various degrees compare to wild-type FGF-21.

TABLE 1

| FGF-21 Mutein | Expression Expression System | In vitro Potency |
| --- | --- | --- |
| Wild-type | *E. coli* | 1.0 |
| Truncated Wild-type* | Yeast | 0.9 |
| Truncated Wild-Type** | HEK293EBNA | 1.3 |
| Wild-type | HEK293EBNA | 0.7 |
| R77E | HEK293EBNA | 1.1 |
| L139E | *E. coli* | 0.1 |
| L146E | *E. coli* | 0.8 |
| Q156E | *E. coli* | 0.6 |
| S163E | *E. coli* | 1.3 |
| I152E/S163E | *E. coli* | 0.9 |
| A145E | *E. coli* | 0.5 |

TABLE 1-continued

| FGF-21 Mutein | Expression Expression System | In vitro Potency |
| --- | --- | --- |
| I152E | *E. coli* | 1.2 |
| L118C/A134C | *E. coli* | 0.4 |
| des-HPIP-L118C/A134C | Yeast | 0.3 |

*truncated by 4 amino acids at the N-terminus, i.e. des-HPIP
**enzymatically truncated by 4-amino acids at the N-terminus by DPP-IV, i.e. des-HPIP

EXAMPLE 5

Ob/ob Mouse Model

A study in an obesity model using male ob/ob mice was done to monitor plasma glucose levels and triglyceride levels after treatment with FGF-21, compared to vehicle and insulin control groups. The test groups of male ob/ob mice (7 weeks old) were injected with vehicle alone (0.9% NaCl), or FGF-21 mutein (0.125 mg/kg) subcutaneously (0.1 mL, once daily) for seven days. Blood was collected by tail clip bleeding on day 7, one hour after the last compound injection and plasma glucose levels were measured using a standard protocol. The ability of the FGF-21 muteins to lower plasma glucose levels as compared to the vehicle control is shown in Table 2. The data in Table 2 indicates that muteins of the present invention lowered plasma glucose levels as compared to vehicle control. The ability of the FGF-21 muteins to lower triglyceride levels as compared to the vehicle control is shown in Table 3.

TABLE 2

| FGF-21 Mutein | Plasma Glucose levels as % of Control |
| --- | --- |
| Wild-type | 60% |
| R77E | 63% |
| Q156E | 65% |
| S163E | 60% |
| A145E | 81% |
| I152E | 82% |
| G161E | 78% |
| L118C-A134C | 80% |

TABLE 3

| FGF-21 Mutein | Triglyceride Levels (mg/dL) |
| --- | --- |
| Experiment #1 | |
| Vehicle Control | 200 |
| Wild-type | 145 |
| R77E | 125 |
| Experiment #2 | |
| Vehicle Control | 165 |
| Wild-type | 90 |
| Q156E | 80 |
| S163E | 70 |
| Experiment #3 | |
| Vehicle Control | 100 |
| Wild-type | 75 |
| A145E | 70 |
| I152E | 60 |
| G161E | 70 |
| L118C-A134C | 75 |

EXAMPLE 6

Pharmaceutical Stability of FGF-21 Muteins

The stability of the FGF-21 muteins of the present invention was analyzed under simulated physiological and pharmaceutical formulation conditions. To simulate physiological conditions, the mutein was analyzed for stability in PBS at room temperature (RT) at a target protein concentration of 10 mg/ml, pH 7.4. Solubility/physical stability of the muteins in PBS is considered satisfactory if recovery of protein following preparation resulted in >90% recovery at RT as determined by size-exclusion and/or reversed-phase chromatography. The muteins of the present invention indicated in Tables 4 and 5 meet this criteria.

It is anticipated that pharmaceutical formulation of a mutein of the present invention will likely be a preserved multi-use formulation, thus, compatibility with a common preservative was analyzed. To test for formulation compatibility, a preservative, m-cresol, (3 mg/mL final concentration, a concentration usually sufficient to meet European Pharmacopia B criteria for preservative effectiveness under neutral pH conditions), was added at room temperature to a solution containing the mutein at approximately 10 mg/ml in PBS, pH 7.4. Physical stability in the presence of preservative was initially accessed by determining protien recovery of the main chromatographic peak after reversed-phase and size exclusion chromatography at RT. Furthermore, the extent of aggregation as measured by DLS (dynamic light scattering) at 37° C. is shown as the average diameter of particles in the presence of m-cresol after two hours, compared to wild-type FGF-21. A larger average diameter corresponds to an increased degree protein association and/or aggregation. The preservative compatibility (as a function average diameter of particulates) of the muteins of the first and second embodiments of the present invention compared to wild-type FGF-21 is shown in Table 4. All muteins were expressed in *E. coli*.

Muteins of the present invention that are stable in PBS and compatible with preservative are designated to have enhanced or improved pharmaceutical properties as compared to wild-type FGF-21. As shown in Table 4, the preferred muteins of the present invention that have enhanced pharmaceutical properties as compared to wild-type FGF-21 are L139E, A145E, L146E, I152E, Q156E, [I152E, S163E], S163E, Q54E, [L21C-L33C, L118C-A134C], L21C-L33C, A26C-K122C, and L118C-A134C.

TABLE 4

| FGF-21 Mutein | Average Particulate Diameter (nm)* |
|---|---|
| Experiment #1 | |
| Wild-type FGF-21 | 1356 |
| Q54E | 210 |
| L139E | 234 |
| A145E | 223 |
| L146E | 248 |
| I152E | 76 |
| Q156E | 353 |
| I152E, S163E | 179 |
| S163E | 154 |
| Experiment #2 | |
| Wild-type FGF-21 | 813 |
| L21C, L33C, L118C, A134C | 10 |
| L21C-L33C | 10 |
| L118C-A134C | 7 |
| A26C-K122C | 7 |

*Average Particulate diameter represents a protein solution at a target conc. of 10 mg/ml, m-cresol at 3 mg/ml, after 2 hours incubation at 37° C.

What is claimed is:

1. A mutein of human FGF-21, consisting of human FGF-21 containing 1 or 2 engineered disulfide bonds wherein said mutein is selected from the group consisting of Leu21Cys-Leu33Cys/Leu118Cys-Ala134Cys-human FGF-21, Leu21Cys/Leu33Cys-human FGF-21, Leu118Cys/Ala134Cys-human FGF-21, or Ala26Cys/Lys122Cys-human FGF-21, wherein the numbering of amino acids is based on SEQ ID NO: 1.

2. A pharmaceutical composition comprising a therapeutically effective amount of a mutein of claim 1 and a pharmaceutically acceptable carrier.

3. A method for lowering blood glucose levels in a patient in need thereof, said method comprising administering to said patient a therapeutically effective amount of a human FGF-21 mutein of claim 1.

4. The method of claim 3, wherein the patient is suffering from obesity, type II diabetes, insulin resistance, hyperinsulinemia, glucose intolerance, hyperglycemia or metabolic syndrome.

5. A biologically active peptide of a mutein of human FGF-21 consisting of human FGF-21 containing 1 or 2 engineered disulfide bonds wherein:

(a) said mutein is selected from the group consisting of Leu21Cys-Leu33Cys/Leu118Cys-Ala134Cys-human FGF-21, Leu21Cys/Leu33Cys-human FGF-21, Leu118Cys/Ala134Cys-human FGF-21, or Ala26Cys/Lys122Cys-human FGF-21, wherein the numbering of amino acids is based on SEQ ID NO:1; and (b) one, two, three, or four amino acids are truncated from the N-terminus.

6. The mutein of claim 5 wherein said mutein is des-(His1Pro2Ile3Pro4)-Leu118Cys/Ala134Cys-human FGF-21.

7. A pharmaceutical composition comprising a therapeutically effective amount of a mutein of claim 6 and a pharmaceutically acceptable carrier.

8. A method for lowering blood glucose levels in a patient in need thereof, said method comprising administering to said patient a therapeutically effective amount of a human FGF-21 mutein of claim 6.

9. The method of claim 8, wherein the patient is suffering from obesity, type II diabetes, insulin resistance, hyperinsulinemia, glucose intolerance, hyperglycemia or metabolic syndrome.

* * * * *